United States Patent
Van Der Kort et al.

(10) Patent No.: US 10,723,678 B2
(45) Date of Patent: Jul. 28, 2020

(54) METHODS FOR USING NITRIC OXIDE TO INHIBIT POPCORN POLYMERIZATION DURING BUTADIENE PROCESSING

(71) Applicant: SABIC Global Technologies B.V., Bergen op Zoom (NL)

(72) Inventors: Theo Van Der Kort, Geleen (NL); Kuldeep Wadhwa, Geleen (NL); Anthoni Van Zijl, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/765,617

(22) PCT Filed: Nov. 8, 2016

(86) PCT No.: PCT/IB2016/056725
§ 371 (c)(1),
(2) Date: Apr. 3, 2018

(87) PCT Pub. No.: WO2017/081611
PCT Pub. Date: May 18, 2017

(65) Prior Publication Data
US 2019/0077731 A1    Mar. 14, 2019

Related U.S. Application Data

(60) Provisional application No. 62/254,606, filed on Nov. 12, 2015.

(51) Int. Cl.
*C07C 7/20* (2006.01)
*C07C 11/167* (2006.01)
(Continued)

(52) U.S. Cl.
CPC .......... *C07C 11/167* (2013.01); *C07C 7/005* (2013.01); *C07C 7/04* (2013.01); *C07C 7/20* (2013.01)

(58) Field of Classification Search
CPC .. C07C 7/005; C07C 7/04; C07C 7/20; C07C 11/167
See application file for complete search history.

(56) References Cited

U.S. PATENT DOCUMENTS

| 3,418,300 A | 12/1968 | Nakajima et al. ............... 526/83 |
| 3,506,636 A | 4/1970 | Sturt ............................. 526/83 |

(Continued)

FOREIGN PATENT DOCUMENTS

| CN | 1328534 A | 12/2001 |
| CN | 102942438 A | 2/2013 |

(Continued)

OTHER PUBLICATIONS

Wang, N-Y et al. (1986) Inorganic Chemistry, 25, 1863-1866.*
(Continued)

*Primary Examiner* — Brian A McCaig
(74) *Attorney, Agent, or Firm* — Norton Rose Fulbright US LLP

(57) ABSTRACT

The presently disclosed subject matter provides a method for inhibiting the formation of popcorn polymer in the vapor phase of a butadiene extraction/purification system. In a non-limiting embodiment, a method for inhibiting the formation of popcorn polymer includes injecting nitric oxide into the upper portion, i.e., headspace of a butadiene distillation column.

17 Claims, 2 Drawing Sheets

(51) Int. Cl.
*C07C 7/00* (2006.01)
*C07C 7/04* (2006.01)

(56) References Cited

U.S. PATENT DOCUMENTS

| | | | |
|---|---|---|---|
| 4,002,554 A | 1/1977 | Borge et al. | 208/48 AA |
| 4,040,912 A | 8/1977 | Watson | 203/9 |
| 4,070,419 A | 1/1978 | Watson | 525/244 |
| 4,247,668 A | 1/1981 | Bracke et al. | 525/313 |
| 4,338,162 A | 7/1982 | Johnson | 203/8 |
| 4,404,413 A | 9/1983 | Haskell | 585/2 |
| 4,538,013 A | 8/1985 | Donike et al. | 585/361 |
| 4,670,131 A | 6/1987 | Ferrell | 208/48 AA |
| 4,754,058 A | 6/1988 | Levy | 560/205 |
| 4,941,926 A | 7/1990 | Nakajima | 134/22.19 |
| 4,956,020 A | 9/1990 | Nakajima | 134/22.19 |
| 5,244,987 A | 9/1993 | Bernard et al. | 526/78 |
| 5,272,231 A | 12/1993 | Campbell et al. | 526/236 |
| 5,345,030 A | 9/1994 | Sun et al. | 585/2 |
| 5,863,994 A | 1/1999 | DeNicola, Jr. et al. | 526/74 |
| 6,562,915 B2 | 5/2003 | Mahling et al. | 526/82 |
| 6,686,422 B2 | 2/2004 | Shahid | 526/82 |
| 6,770,222 B1 | 8/2004 | Ukita et al. | 252/399 |
| 7,135,594 B2 | 11/2006 | Yada et al. | 560/205 |

FOREIGN PATENT DOCUMENTS

| | | |
|---|---|---|
| EP | 0301879 A2 | 2/1989 |
| GB | 744504 A | 2/1956 |
| GB | 798347 A | 7/1958 |
| GB | 1265419 A | 3/1972 |
| GB | 1472859 A | 5/1977 |
| JP | 50035048 B1 | 11/1975 |
| JP | 2004099858 A | 4/2004 |
| RU | 2243201 C1 | 12/2004 |
| SU | 411682 A3 | 1/1974 |
| WO | WO1998020045 A1 | 5/1998 |

OTHER PUBLICATIONS

Abuin, E. et al. (1978) International Journal of Chemical Kinetics, X, 677-686 [Office action only references p. 677].*
Written Opinion and International Search Report from PCT/IB2016/056725, dated Jan. 31, 2017, 10 pages.
*Concise Dictionary of Fine Chemicals*, compiled by Wu Shimin and Yin Delin, Liaoning Science and Technology Press, published on Jun. 30, 1999, p. 418.
*Paint Auxiliaries*, compiled by Qian Fenglin and Zhu Yushu, Chemical Industry Press, published on Nov. 30, 1990, p. 173.

* cited by examiner

100

Providing a hydrocarbon stream containing 1,3-butadiene to a distillation unit — 101

Injecting nitric oxide into the distillation unit containing the 1,3-butadiene hydrocarbon stream — 102

Distilling 1,3-butadiene from the hydrocarbon stream — 103

Flask 1: No Inhibitor    Flask 2: 100 ppm OH-TEMPO    Flask 3: Nitric Oxide

METHODS FOR USING NITRIC OXIDE TO INHIBIT POPCORN POLYMERIZATION DURING BUTADIENE PROCESSING

CROSS-REFERENCE TO RELATED APPLICATIONS

This application is a national phase application under 35 U.S.C. § 371 of International Application No. PCT/IB2016/056725 filed Nov. 8, 2016, which claims priority to U.S. Provisional Patent Application No. 62/254,606 filed Nov. 12, 2015. The entire contents of each of the above-referenced disclosures is specifically incorporated by reference herein without disclaimer.

FIELD

The presently disclosed subject matter relates to methods for mitigating popcorn polymerization of 1,3-butadiene during extraction and purification.

BACKGROUND 1,3-butadiene is a simple conjugated diene. It is a product of the petrochemical industry, used as a monomer starting material for the preparation of various polymers, including synthetic rubbers. 1,3-butadiene is often produced commercially by one of three processes: steam cracking of paraffinic hydrocarbons; catalytic dehydrogenation of n-Butane and n-Butene; or oxidative dehydrogenation of n-Butene. The product of these processes is known as crude 1,3-butadiene, which contains propyne, 1,2-butadiene, and C5 hydrocarbons, as well as other compounds. This crude 1,3-butadiene can then be further purified using a distillation process. Purification methods of crude 1,3-butadiene are commonly known, and typically involve a series of two distillation columns. In such methods, crude 1,3-butadiene is fed into the first distillation column. Propyne can be removed as an overhead gas from the top of the first column, while the bottoms, containing 1,3-butadiene, 1,2-butadiene, and C5 hydrocarbons are sent to a second butadiene distillation column. The purified 1,3-butadiene product is withdrawn as a liquid from the top of the second column, and the 1,2-butadiene and C5 hydrocarbons are removed as a liquid from the bottom of the second column.

One common problem found in certain butadiene extraction systems is the formation of butadiene polymer, commonly identified as popcorn polymer. Polymerization occurs where monomers react spontaneously to form polymer chains. Popcorn polymer can form in both the liquid and vapor phase, but is most likely to form in the vapor spaces where the concentrations of olefins and temperature are both very high. Formation and growth of popcorn polymer is often accelerated by external factors such as oxygen and iron oxide (a by-product of corrosion). The rapid expansion rate of popcorn polymer creates significant concerns for processing equipment. If uncontrolled, the growth of popcorn polymer may result in the clogging of processing equipment or piping, and may even lead to equipment rupture or fracture due to mechanical pressure.

Certain methods for inhibiting polymer formation for reactive monomers are known in the art. G.B. Patent No. 1,472,859 discloses the introduction of nitric oxide prior to distillation of C4 to C5 diolefins in order to reduce fouling by "rubber-like" deposits, i.e., polymer. This method can include purging the nitric oxide from the unit prior to its use. U.S. Pat. Nos. 4,754,058, 4,338,162, and G.B. Patent No. 798,347 disclose methods to inhibit polymerization by adding nitric oxide during distillation of reactive monomers. U.S. Pat. No. 4,404,413 discloses treatment of butadiene with carbon disulfide or elemental phosphorous. U.S. Pat. No. 5,345,030 discloses the use of sulfur-containing compounds as inhibitors of the polymerization of olefinically unsaturated monomers. U.S. Pat. No. 6,686,422 discloses the use of nitroxides to inhibit polymerization of olefins. U.S. Pat. No. 4,956,020 discloses the use of nitroso compounds to prevent popcorn polymer formation. U.S. Pat. No. 4,941,926 discloses the treatment of an olefin production apparatus with acetic acid-based compounds to prevent popcorn polymer formation.

A drawback of certain methods for inhibiting popcorn polymerization of butadiene is that the inhibitors are only effective in solution phase due to their high molecular weight. Formation of popcorn polymer however can be observed in the gaseous phase of a butadiene unit. There is a need for methods for inhibiting popcorn polymerization which are effective in the vapor phase of a butadiene distillation unit.

SUMMARY OF THE DISCLOSED SUBJECT MATTER

The presently disclosed subject matter provides methods for inhibiting popcorn polymer formation during butadiene distillation. In certain embodiments, the present disclosure provides methods for inhibiting the formation of popcorn polymer in the vapor phase of a butadiene extraction/purification system.

In certain embodiments, a method for inhibiting the formation of popcorn polymer in the vapor phase of a butadiene extraction/purification system can include providing a hydrocarbon stream containing 1,3-butadiene to a distillation unit. The method can further include injecting nitric oxide into the distillation unit containing the hydrocarbon stream to reduce 1,3-butadiene polymerization. In certain embodiments, the nitric oxide can be injected into the upper portion of the distillation unit, i.e., the headspace of the distillation unit. In certain embodiments, the temperature within the headspace of the distillation unit can be between about 40° C. and 70° C. For example but not by way of limitation, the temperature can be about 60° C. The method can further include distilling 1,3-butadiene from the hydrocarbon stream.

In certain embodiments, the amount of nitric oxide injected into the distillation unit can saturate the system. In certain embodiments, the nitric oxide can have a concentration of at least about 100 parts per million.

In certain embodiments, the nitric oxide can be injected into the butadiene distillation unit at a rate of about 0.005 to about 0.01 gm/min.

In certain embodiments, the nitric oxide can remain in the gaseous phase.

In certain embodiments, the nitric oxide can be injected into the distillation unit continuously during the distilling of 1,3-butadiene from the hydrocarbon stream.

In certain embodiments, the nitric oxide can be injected into the distillation unit intermittently during the distillation of 1,3-butadiene from the hydrocarbon stream.

In certain embodiments, the nitric oxide can be injected into the distillation unit concomitantly with the hydrocarbon stream containing 1,3-butadiene.

In certain embodiments, the nitric oxide can remain unpurged from the distillation unit prior to the addition of the hydrocarbon stream containing 1,3-butadiene into the unit.

DETAILED DESCRIPTION

The presently disclosed subject matter provides methods for inhibiting the formation of popcorn polymer in the vapor phase of a butadiene extraction/purification system. In certain embodiments, the methods of the present disclosure can inhibit the formation of popcorn polymer by injecting nitric oxide into a butadiene distillation unit. In certain embodiments, the nitric oxide can be injected into the upper portion, i.e., headspace of the butadiene distillation unit.

Figure 1:
FIG. 1 is a schematic diagram depicting an exemplary method in accordance with one non-limiting embodiment of the disclosed subject matter.
Figure 1:

For the purpose of illustration and not limitation, FIG. 1 is a schematic diagram depicting an exemplary method for inhibiting popcorn polymer formation during the separation of 1,3-butadiene in accordance with one non-limiting embodiment of the disclosed subject matter.

As shown in FIG. 1, the method 100 can include providing a hydrocarbon feed stream from which 1,3-butadiene can be extracted and/or purified. In certain embodiments the hydrocarbon stream can contain olefins, paraffins, and 1,3-butadiene. For example, but not by way of limitation, the hydrocarbon stream can contain 1,3-butadiene, as well as various impurities, including 1,2-butadiene, cis-2-butene, trans-2-butene, butane, isobutane, propylene, propane, propyne, or combinations thereof.

The method can further include injecting the 1,3-butadiene hydrocarbon feed stream into a butadiene distillation unit. In certain embodiments, the butadiene distillation unit can include at least one distillation column. For example, but not by limitation, the butadiene distillation unit can include a fractionator distillation/purification column. Alternatively, the distillation unit can include a reactive distillation column.

The method can further include injecting a nitric oxide feed stream into the distillation unit. In certain embodiments, the nitric oxide can be injected as a gas into the headspace of the distillation unit and will remain in a gaseous state. In certain embodiments, the amount of nitric oxide injected into the distillation unit can saturate the system. In certain embodiments, the concentration of the nitric oxide feed stream can be about 100 to 500 parts per million. In certain embodiments, the nitric acid can inhibit the formation of popcorn polymer within the vapor space of the distillation unit.

The method can further include distilling 1,3-butadiene from the hydrocarbon stream via methods known in the art.

In certain embodiments, the nitric oxide feed stream can be added continuously throughout the butadiene distillation process. Alternatively, in certain embodiments, the nitric oxide feed stream can be added intermittently throughout the butadiene distillation process.

In certain embodiments, the nitric oxide feed stream can be added prior to the addition of the 1,3-butadiene hydrocarbon feed stream. Alternatively, in certain embodiments, the nitric oxide feed stream can be added concomitantly with the 1,3-butadiene hydrocarbon stream.

In certain embodiments, the pressure within the butadiene distillation unit can be in a range from about 3 bar to 8 bar. The temperatures within the butadiene distillation unit can be in a range between about 40° C. and about 70° C. By way of non-limiting example, the temperature within the top portion of the butadiene distillation unit can be about 60° C.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5% and/or up to 1% of a given value.

The following example is merely illustrative of the presently disclosed subject matter and should not be considered as a limitation in any way.

EXAMPLE

This example illustrates the efficiency of nitric oxide as a polymerization inhibitor.

In this example, styrene was selected as a reactive monomer because of its similar reactivity compared to butadiene radical polymerization and for its ease of handling.

Figure 2:
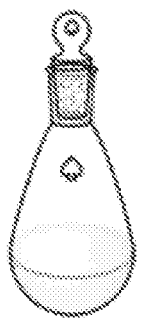
FIG. 2 is a schematic diagram depicting a laboratory experiment providing a non-limiting example of the disclosed subject matter.
Figure 2:
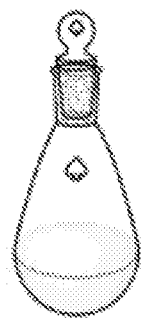
Figure 2:
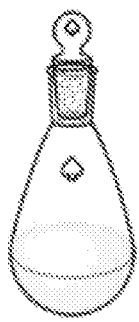

In this example, 10 ml of purified styrene was added to three sealed penicillin flasks (Flasks 1, 2, and 3) and each flask was purged with nitrogen to remove any traces of oxygen. For the purpose of illustration, FIG. 2 is a schematic diagram depicting the flasks that were used in this example. Flask 1 contained no inhibitor and was used as a blank. OH-TEMPO, a commercially used polymerization inhibitor was added to Flask 2 at 100 parts per million dosage. Flask 3 was purged with >99% nitric oxide gas. Flasks 1, 2 and 3 were heated to 60° C. for a duration of 90 minutes. After 90 minutes, all three reactions were quenched by lowering the temperature immediately to 2° C. to stop any polymerization.

After the reaction was stopped, gel permeation chromatography (GPC) was used to determine the polymer content and molecular weight distributions in all three flasks. The results are set forth in Table 1.

TABLE 1

| Polymerization Inhibitor Example Using OH-TEMPO and Nitric Oxide | | | | |
|---|---|---|---|---|
| Flask No. | External Additive | Dosage | Polymer Content* | Mn* |
| 1 | None | — | 4.3 g/l | 805646 |
| 2 | OH-TEMPO | 100 ppm | Not Detected | |
| 3 | Nitric Oxide | Saturated | Not Detected | 263** |

*Average of two runs
**2.0 g/l of low molecular weight oligomers were detected

This study indicates the efficiency of nitric oxide as a gas phase inhibitor for polymerization at 60° C.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

The invention claimed is:

1. A method for reducing 1,3-butadiene polymerization during distillation of a 1,3-butadiene containing stream, the method comprising:
   (a) providing a hydrocarbon stream comprising 1,3-butadiene to a distillation unit, wherein the distillation unit comprises a headspace;
   (b) intermittently injecting a polymerization inhibitor consisting of gaseous nitric oxide into the distillation unit containing the hydrocarbon stream in an amount sufficient to reduce 1,3-butadiene polymerization; and distilling 1,3-butadiene from the hydrocarbon stream.

2. The method of claim 1, wherein the gaseous nitric oxide is injected into the distillation unit at 0.005 gm/min.

3. The method of claim 2, wherein the nitric oxide is injected into the headspace.

4. The method of claim 2, wherein the gaseous nitric oxide is injected into the distillation unit at 0.01 gm/min.

5. The method of claim 2, wherein the nitric oxide is intermittently injected into the distillation unit concomitantly with the hydrocarbon stream containing 1,3-butadiene.

6. The method of claim 2, wherein the nitric oxide is not purged from the distillation unit prior to the addition of the hydrocarbon stream containing 1,3-butadiene into the unit.

7. The method of claim 1, wherein the gaseous nitric oxide is injected into the headspace.

8. The method of claim 1, wherein the gaseous nitric oxide is injected into the distillation unit at 0.005 gm/min.

9. The method of claim 1, wherein the gaseous nitric oxide is not purged from the distillation unit prior to the addition of the hydrocarbon stream containing 1,3-butadiene into the unit.

10. The method of claim 1, wherein the gaseous nitric oxide is injected into the distillation unit at a range of about 0.005 to about 0.01 gm/min.

11. The method of claim 1, wherein the gaseous nitric oxide is injected into the headspace.

12. A method for reducing 1,3-butadiene polymerization during distillation of a 1,3-butadiene containing stream, the method comprising:
   (a) providing a hydrocarbon stream comprising 1,3-butadiene to a distillation unit, wherein the distillation unit comprises a headspace;
   (b) intermittently injecting a composition consisting of polymerization inhibitor into the distillation unit containing the hydrocarbon stream at a concentration of at least about 100 parts per million to reduce 1,3-butadiene polymerization; and distilling 1,3-butadiene from the hydrocarbon stream;
wherein the polymerization inhibitor is gaseous nitric oxide.

13. A method for reducing 1,3-butadiene polymerization during distillation of a 1,3-butadiene containing stream, the method comprising:
   (a) providing a hydrocarbon stream comprising 1,3-butadiene to a distillation unit, wherein the distillation unit comprises a headspace;
   (b) intermittently injecting a polymerization inhibitor consisting of gaseous nitric oxide into the distillation unit containing the hydrocarbon stream to reduce 1,3-butadiene polymerization; and
   (c) distilling 1,3-butadiene from the hydrocarbon stream, wherein the nitric oxide is injected into the distillation unit during the distillation of 1,3-butadiene from the hydrocarbon stream.

14. The method of claim 13, wherein the nitric oxide is injected into the headspace.

15. A method for reducing 1,3-butadiene polymerization during distillation of a 1,3-butadiene containing stream, the method comprising:
   (a) providing a hydrocarbon stream comprising 1,3-butadiene to a distillation unit, wherein the distillation unit comprises a headspace;
   (b) intermittently injecting a polymerization inhibitor consisting of gaseous nitric oxide into the distillation unit containing the hydrocarbon stream at a concentration of at least about 100 parts per million to reduce 1,3-butadiene polymerization; and
   (c) distilling 1,3-butadiene from the hydrocarbon stream, wherein the nitric oxide is intermittently injected into the distillation unit during the distillation of 1,3-butadiene from the hydrocarbon stream.

16. The method of claim 15, wherein the gaseous nitric oxide is intermittently injected into the distillation unit at a range of about 0.005 to about 0.01 gm/min.

17. The method of claim 15, wherein the polymerization inhibitor is injected into the headspace.

* * * * *